United States Patent [19]

Scheuffgen

[11] Patent Number: 4,868,220

[45] Date of Patent: Sep. 19, 1989

[54] LANOLIN SUBSTITUTE AND COMPOSITION CONTAINING THE SAME

[75] Inventor: Ingeborg Scheuffgen, Neuss, Fed. Rep. of Germany

[73] Assignee: Henkel Kommanditgsellschaft and Aktien, Duesseldorf, Fed. Rep. of Germany

[21] Appl. No.: 898,739

[22] Filed: Aug. 15, 1986

Related U.S. Application Data

[63] Continuation of Ser. No. 423,277, Sep. 24, 1982, abandoned.

[30] Foreign Application Priority Data

Apr. 23, 1982 [DE] Fed. Rep. of Germany ....... 3215912

[51] Int. Cl.$^4$ .......................... A61K 7/40; A61K 7/48
[52] U.S. Cl. ..................................... 514/784; 514/785; 514/786; 514/844; 514/846; 514/847
[58] Field of Search ............... 514/784, 785, 786, 844, 514/846, 847

[56] References Cited

U.S. PATENT DOCUMENTS

| | | | |
|---|---|---|---|
| 3,102,128 | 8/1963 | Hennig et al. | 424/365 |
| 4,066,789 | 1/1978 | Mores et al. | 424/365 |
| 4,143,160 | 3/1979 | Osberghaus et al. | 424/365 |
| 4,153,726 | 5/1979 | Borggrefe et al. | 424/365 |
| 4,216,201 | 8/1980 | Calvo | 424/365 |
| 4,272,544 | 6/1981 | Cella et al. | 424/365 |
| 4,375,480 | 3/1983 | Soma | 424/365 |
| 4,382,960 | 5/1983 | Flom | 424/365 |

FOREIGN PATENT DOCUMENTS

| | | | |
|---|---|---|---|
| 2511644 | 9/1976 | Fed. Rep. of Germany | 424/365 |
| 1396613 | 3/1965 | France | 424/365 |
| 54-35220 | 3/1979 | Japan | 424/365 |
| 55-31037 | 3/1980 | Japan | 424/365 |
| 56-104807 | 8/1981 | Japan | 424/365 |

OTHER PUBLICATIONS

*The Merck Index,* 9th edition, Abst. #9422, (1976).
Edward Sagarin, Cosmetics Science and Technology, Interscience Publishers, 1966, pp. 154–157.
Ralph G. Harry, Harry's Cosmeticology, Leonard Hill Books, 1973, p. 55.

*Primary Examiner*—Dale R. Ore
*Attorney, Agent, or Firm*—Ernie G. Szoke; Wayne C. Jaeschke; Henry F. Millson, Jr.

[57] ABSTRACT

A substitute for lanolin which comprises 40 to 60% by weight of a mixed ester of about equimolar amounts of a di-fatty acid ester of pentaerythritol and a di-fatty alcohol citrate, 20 to 45% by weight of monoglycerides and diglycerides of oleic acid, 3 to 10% by weight of the monoglycerides and diglycerides of palmitic acid and stearic acid and 3 to 10% by weight of an adduct of 3 to 7 mols of ethylene oxide onto vegetable sterol and compositions in which it is included.

2 Claims, No Drawings

LANOLIN SUBSTITUTE AND COMPOSITION CONTAINING THE SAME

This application is a continuation of co-pending U.S. patent application Ser. No. 423,277, filed Sept. 24, 1982, now abandoned.

BACKGROUND OF THE INVENTION

The subject of the invention is a novel substitute for lanolin, consisting of a mixture of synthetic surface-active materials derived from fatty products and its use for the preparation of cosmetic and pharmaceutical ointments, creams, emulsions and stick products.

Lanolin is a known component in the preparation of cosmetic compositions. Its refined and deacidified form as well as various of its derivatives are used for the preparation of emulsions and stick products. Its composition is highly complex and only partly identified. To a large part it consists of esters of long-chain carboxylic acids and hydroxycarboxylic acids with cholesterol and lanosterol. Lanolin is valued especially as emulsifying agent, stabilizer and co-emulsifying agent because of its high water absorbing capacity, and as an emollient in ointments and stick preparations because of its skin softening characteristics. Despite the described advantages, however, lanolin also has certain disadvantages. For example, allergic reactions have been reported when using cosmetics containing lanolin and which were said to have been caused by certain pesticide residues and polycyclic alcohols present in the natural product. This is the reason for requiring information about the lanolin content on the label according to the cosmetics regulations of 1977 in Germany. Another disadvantage of the natural product is that it has a pronounced odor which requires stronger masking perfume, which sometimes is not well tolerated by persons with sensitive skin or a tendency to allergic reactions. Besides, as a natural product, lanolin is subject to considerable variations in quality, price and supply. These reasons alone make a synthetic substitute desirable. The chemical synthesis of lanolin is impossible because of its complex composition. Attempts at creating useful, technologically comparable alternatives so far have resulted in unsatisfactory substitutes, which cannot compare with the natural product either with respect to its emulsifying capabilities or its skin-softening characteristics. Consequently there existed the problem of creating a synthetic substitute for lanolin resembling as closely as possible the natural product in its commercial application and cosmetic characteristics.

OBJECTS OF THE INVENTION

It is an object of the invention to provide a substitute for lanolin.

Another object of the invention is to provide a lanolin substitute which has predetermined and reproducible characteristics.

A further object is to provide a lanolin substitute which is hypoallergenic.

Another object is to improve compositions of cosmetic and pharmaceutical ointments, creams, emulsions and stick products by using the lanolin substitute as an ingredient.

A further object is to provide a lanolin substitute which comprises 40 to 60% by wt. of a mixed ester of about equimolar amounts of a di-fatty acid ester of pentaerythritol and a di-fatty alchohol citrate, 20 to 45% by wt. of monoglycerides and diglycerides of oleic acid, 3 to 10% by wt. of the monoglycerides and the diglycerides of palmitic acid and stearic acid and 3 to 10% by wt. of an adduct of 3 to 7 mols ethylene oxide and a vegetable sterol.

DESCRIPTION OF THE INVENTION

The problem was solved by combining well-known, synthetic, surface-active materials derived from fatty products which offers, within relatively narrow, quantitative ratios, the desired lanolin-like characteristics, particularly a comparable consistency, a comparable stability in cosmetic emulsions and creams and a similarly good feeling on the skin of products which include it. The composition according to the invention is characterized by a content of 40 to 60% by wt. of a mixed ester of about equimolar amounts of a di-fatty acid ester of pentaerythritol and a di-fatty alchohol citrate 25 to 45% by wt. of a mixture of monoglycerides and diglycerides of oleic acid 3 to 10% by wt. of a mixture of the monoglycerides and the glycerides of palmitic and/or stearic acid 3 to 10% by wt. of the adduct of 3 to 7 mols of ethylene oxide and a vegetable sterol.

The mixed esters of about equimolar amounts of pentaerythritol di-fatty acid ester and di-fatty alcohol citrate to be used in the combination according to the invention have been described in German patent specification No. 1,165,575. Of the products mentioned in this publication, the mixed ester of a di-coconut fatty acid ester of pentaerythritol and a di-octadecyl citrate described there in Example 1 is especially suitable for the preparation of the lanolin substitute of the invention.

The monoglycerides and diglycerides of oleic acid to be used in the lanolin substitute composition of the invention are products that can be obtained, e.g., by the esterification of glycerol with 1 to 2 mols of an olein, i.e., a fatty acid consisting mainly of oleic acid. Such products generally consist of mixtures of the monoester, diester and triester.

The monoester should be at least 40% by weight of the mixture.

The monoglycerides and diglycerides of palmitic and/or stearic acid to be used in the compositions of the invention are products that can be prepared, e.g., by the esterification of glycerol with 1 to 2 mols of a technical grade stearin, i.e. a fatty acid consisting mainly of palmitic acid and stearic acid. Such products also consist of monoesters, diesters and triesters. The content of monoester should be at least approx. 40% by weight of the mixture.

The adduct of ethylene oxide and a vegetable sterol to be used in the lanolin substitute compositions of the invention is prepared by the reaction of the sterol with 3 to 7 mols ethylene oxide preferably in the presence of a basic catalyst, e.g. potassium hydroxide or sodium methylate, under pressure. Suitable as vegetable sterol is, e.g., the refined sterol mixture isolated from the unsaponifiable part of vegetable oils. These are mixtures of various sterol compounds with lesser amounts of unknown accompanying substances of vegetable origin. Defined constituents of such vegetable sterols are, for example, sitosterol, campesterol, stigmasterol, brassicasterol, α-spinasterol, seagasterol and fucosterol at varying quantitative ratios. Preferably suitable is the adduct of about 5 mols ethylene oxide and the refined soysterol.

But especially suitable and universally useable as lanolin substitute is a composition comprising:

about 50% by wt. of the mixed esters of equimolar amounts of dicononut fatty acid ester of pentaerythritol and di-n-octadecyl citrate, about 40% by wt. of a mixture of monoglycerides and diglycerides of oleic acid with about 46% by wt. of monoglyceride content, about 5% by wt. of a mixture of the monoglycerides and diglycerides of palmitic and stearic acid with about 46% by wt. of monoglyceride content and about 5% by wt. of the adduct of 5 mols ethylene oxide and refined soysterol.

This preferred composition has a consistency similar to natural lanolin and its technical analytical data are quite close to those of the natural product. But most important, the creams, ointments and lotions prepared with it, regardless of whether they are of the water-in-oil or the oil-in-water type, have a similar characteristics with regard to dispersion, smoothness, suppleness, gloss or transparency when compared with compositions prepared with natural lanolin. In addition, the products have a very similar viscosity range and show practically no differences in storage stability, when corresponding formulations prepared with lanolin are compared with those of the invention.

The lanolin substitutes of the invention also have the advantage that their use in cosmetic and pharmaceutical preparations results in products which are hypoallergenic. Since the new lanolin substitutes are almost odorless, they permit the sparing use of perfume in compositions prepared with them. This contributes to improved tolerance of cosmetics on the skin of sensitive persons.

The lanolin substitutes of the invention are compatible with the other conventional ingredients in cosmetic ointments, creams, lotions and stick preparations. They thus can be combined with all known adjuvants without problems. Such adjuvants are, e.g., anionic and non-ionic emulsifying agents or ointment bases, soaps and cosmetic fatty materials such as vaseline, liquid paraffins, solid paraffins, microwaxes, triglyceride oils, waxes (e.g. spermaceti, bees wax), fatty alcohols, fatty acids, fatty acid esters, glycerol, perfume oils, preservatives, etc.

The following examples are given by way of explanation and not by way of limitation.

EXAMPLES

1. Characterization of the emulsifying components used in the examples:

1.1 Mixed Ester

A mixed ester of di-octadecyl citrate and di-coconut fatty acid ester of pentaerythritol was prepared as set forth in DE-PS 1,165,574, Example 1c. The reesterification product had the following analytical data:
    Acid number: 0.8
    saponification number: 226
    hydroxyl number : 71

1.2 A mixture of the monoglycerides and diglycerides of Oleic Acid

The product used was prepared from technical grade oleic acid (acid number 202, iodine number 92, turbidity point 6° C.) and had the following analytical data:
    saponification number: 177
    iodine number: 74
    monoglyceride content: 46%
    free glycerol: appox. 1%

1.3 A mixture of the monoglycerides and diglycerides of Palmitic and Stearic Acid The product used was prepared from technical grade stearin (1% $C_{12}$, 2% $C_{14}$, 45% $C_{16}$, 2% $C_{17}$, 47% $C_{18}$, iodine number 0.5) and had the following analytical data:
    saponification number: 171
    rising melting point: 58° C.
    monoglyceride content: 46%
    free glycerin: approx. 1%

1.4 Ethoxylated Soysterol

The product used was prepared from a refined soysterol and 5 mols ethylene oxide by addition reaction and had the following analytical data:
    hydroxyl number: approx. 100
    melting range: 70°-90° C.
    free sterol: approx. 10% (gas chromatography)

| 2. Lanolin Substitute of the invention | | Natural lanolin (anhydrous) for comparison |
|---|---|---|
| mixed ester according to 1.: | 50% by wt. | |
| mono-diglyceride of oleic according to 1.2: | 40% by wt. | |
| mono-diglyceride of steraric acid according to 1.3: | 5% by wt. | according to Deutsches Arzneibuch, 8th edition, 1978 |
| adduct of 5 mols ethylene and soysterol | 5% by wt. | |
| Technical analytical data: | | |
| acid number | 3.8 | 0.8-2.0 |
| saponification number | 186 | 90-105 |
| iodine number | 33 | 18-32 |
| hydroxyl number | 151 | — |
| melting point | 37° C. | 36-42° C. |
| 3. Test Formulations (in parts by weight) | | |
| 3.1 Liquid Hand Lotion (O/W-Emulsion) | | |
| Lanolin | — | 5 |
| lanolin substitute of (Example 2) | 5 | — |
| O/W-base (EMULGADE F ®)[1] | 2 | 2 |
| stearin (50% $C_{16}$, 50% $C_{18}$) | 2 | 2 |
| liquid paraffin, viscous | 2.5 | 2.5 |
| decyl oleate (CETIOL V ®) | 3 | 3 |
| olive oil | 1.5 | 1.5 |

-continued

| | | |
|---|---|---|
| triethanolamine | 1 | 1 |
| water | 83 | 83 |
| emulsification | good | good |
| structure, appearance | | |
| after preparation | smooth, glossy | smooth, glossy |
| after 8 weeks at 20° C. | smooth, glossy | smooth, glossy |
| after 8 weeks at 40° C. | smooth, glossy | smooth, glossy |
| viscosity (20° C.)[2] | | |
| after 1 day | 37 Pa.s | 66 Pa.s |
| after 8 weeks | 43 Pa.s | 77 Pa.s |
| 3.2 Sports Cream (W/O-Emulsion) | | |
| lanolin | — | 5 |
| lanolin substitute (according to 2.) | 5 | — |
| W/O-base (PROTEGIN ®)[3] | 20 | 20 |
| microwax | 2.5 | 2.5 |
| VASELINE ® Petroleum Jelly (white), available from Chesebrough-Ponds, Inc. | 2.5 | 2.5 |
| liquid paraffin | 2.5 | 2.5 |
| $MgSO_4 \cdot 7 H_2O$ | 0.4 | 0.4 |
| glycerol | 2.0 | 2.0 |
| water | 65.1 | 65.1 |
| emulsification | good | good |
| structure, appearance | | |
| after preparation | smooth, glossy | smooth, glossy |
| after 8 weeks at 20° C. | smooth, glossy | smooth, glossy |
| after 8 weeks at 40° C. | slightly gritty | smooth, glossy |
| viscosity (20° C.) | | |
| after 1 day | 600 Pa.s | 225 Pa.s |
| after 8 weeks | 450 Pa.s | 200 Pa.s |
| 3.3 Stearate Cream (O/W Emulsion) | | |
| lanolin | — | 2 |
| lanolin substitute (according to 2.) | 2 | — |
| stearin (50% $C_{16}$, 50% $C_{18}$) | 14 | 14 |
| cetyl alcohol | 3 | 3 |
| liquid paraffin | 1 | 1 |
| glycerol | 2 | 2 |
| aminomethylpropane diol | 1 | 1 |
| water | 77 | 77 |
| emulsification | good | good |
| structure, appearance | | |
| after preparation | smooth, glossy | slightly yellow glossy |
| after 8 weeks | slightly inhomogeneous | slightly inhomogeneous |
| viscosity (20° C.) | | |
| after 1 day | 275 Pa.s | 650 Pa.s |
| after 8 weeks | 287 Pa.s | 487 Pa.s |
| 3.4 Vanishing Cream (O/W-Emulsion) | | |
| lanolin | — | 2 |
| lanolin substitute (according to 2.) | 2 | — |
| O/W-cream base (TEGIN ®)[4] | 12 | 12 |
| cetyl alcohol | 1 | 1 |
| olive oil | 3 | 3 |
| glycerol | 5 | 5 |
| water | 77 | 77 |
| emulsification | good | good |
| structure, appearance | | |
| after preparation | smooth, glossy | smooth, glossy |
| after 8 weeks at 20° C. | smooth, glossy | smooth, glossy |
| after 8 weeks at 40° C. | slightly inhomogeneous | slightly inhomogeneous |
| viscosity (20° C.) | | |
| after 1 day | 125 Pa.s | 125 Pa.s |
| after 8 weeks | 150 Pa.s | 157 Pa.s |
| 3.5 Skin Cream, anhydrous | | |
| lanolin | — | 10 |
| lanolin substitute (of Example 2.) | 10 | — |
| cetyl alcohol | 10 | 10 |
| decyl oleate (CETIOL V ®) | 25 | 25 |
| VASELINE ® petroleum jelly (white) | 35 | 35 |
| solid paraffin (52° C.) | 5 | 5 |
| bees wax, white | 15 | 15 |
| structure and appearance | | |
| after preparation | smooth and firm | smooth and firm |
| after 8 weeks at 20° C. | smooth and firm | smooth and firm |
| after 8 weeks at 40° C. | smooth and firm | smooth and firm |
| 3.6 Nutrient Cream (O/W-Emulsion) | | |
| lanolin | — | 3 |
| lanolin substitute (of Example 2) | 3 | — |

| | -continued | |
|---|---|---|
| cetyl alcohol | 1.5 | 1.5 |
| stearin (50% $C_{16}$, 50% $C_{18}$) | 12 | 12 |
| 2-octyldodecanol (EUTANOL G ®)[5] available from Henkel KGaA | 12 | 12 |
| caprylic-capric acid triglyceride (MYRITOL 318 ®)[6] | 6 | 6 |
| bees wax, white | 2 | 2 |
| liquid paraffin, viscous | 5 | 5 |
| glycerol | 6 | 6 |
| triethanolamine | 1.5 | 1.5 |
| water | 51.0 | 51.0 |
| emulsification | good | good |
| structure and appearance | | |
| after preparation | smooth, glossy | smooth, glossy |
| after 8 weeks at 20° C. | slightly inhomogeneous | slightly inhomogeneous |
| after 8 weeks at 40° C. | smooth, stable | smooth, stable |
| viscosity (20° C.) | | |
| after 1 day | 425 Pa.s | 275 Pa.s |
| after 8 weeks | 412 Pa.s | 462 Pa.s |
| 3.7 Baby Cream (O/W-Emulsion) | | |
| lanolin | — | 10 |
| lanolin substitute (of Example 2.) | 10 | — |
| mono-diglyceride of palmitic/ stearic acid (CUTINA MD ®)[7] | 16 | 16 |
| cetyl-stearyl alcohol polyglycol ether (12 EO) | 3 | 3 |
| decyl oleate (CETIOL V ®) | 10 | 10 |
| triglyceride of caprylic-capric acid (MYRITOL 318 ®) | 4 | 4 |
| calendula oil | 3 | 3 |
| water | 54 | 54 |
| Emulsification | good | good |
| structure and appearance | | |
| after preparation | smooth, slightly dull | smooth, slightly dull |
| after 8 weeks at 20° C. | slightly inhomogeneous | smooth slightly dull |
| after 8 weeks at 40° C. | slightly inhomogeneous | slightly inhomogeneous |
| viscosity (20° C.) | | |
| after 1 day | 437 Pa.s | 350 Pa.s |
| after 8 weeks | 437 Pa.s | 387 Pa.s |
| 3.8 Baby Cream (W/O-Emulsion) | | |
| lanolin | — | 5 |
| lanolin substitute (of Example 2) | 5 | — |
| W/O-emulsifying agent (DEHYMULS E ®)[8] | 7 | 7 |
| decyl oleate (CETIOL V ®) | 10 | 10 |
| VASELINE ® petroleum jelly (white) | 15 | 15 |
| talc | 15 | 15 |
| zinc oxide | 10 | 10 |
| water | 38 | 38 |
| emulsification | good | good |
| structure and appearance | | |
| after preparation | soft, glossy | soft, glossy |
| after 8 weeks at 20° C. | soft, glossy | soft, glossy |
| after 8 weeks at 40° C. | soft, glossy | soft, glossy |
| viscosity (20° C.) | | |
| after 1 day | 725 Pa.s | 400 Pa.s |
| after 8 weeks | 735 Pa.S | 675 Pa.s |

[1] Colloidally dispersed mixture of cetyl-stearyl alcohol, sodium cetylstearyl sulfate and nonionic emulsifying agents, available from Henkel KGaA.
[2] A Brookfield rotation viscosimeter was used to determine the viscosity.
[3] Mixture of various nonionic emulsifying agents, sterols, aliphatic alcohols, fatty acids, esters, waxes and paraffin hydrocarbons; manufacturer; Goldschmidt AG, Essen
[4] Glycerol mono distearate, manufacturer: Goldschmidt AG, Essen
[5] Glycerol distearate octyldodecanol, available from Henkel KGaA.
[6] Caprylic/capric triglyceride, available from Henkel KGaA.
[7] Glyceryl stearate, available from Henkel KGaA.
[8] Mixture of sorbitan sesquioleate, beeswax, and aluminum stearate, available from Henkel KGaA.

The preceding specific embodiments are illustrated of the practice of the invention. It is to be understood, however, that other expedients known to those skilled in the art or disclosed herein, may be employed without departing from the spirit of the invention or the scope of the appended claims.

I claim:
1. A lanolin substitute which comprises
(a) about 50% by wt. of a mixture of about equimolar amounts of dicoconut acid ester of pentaerythritol and di-n-octadecyl citrate;

(b) about 40% by wt. of a mixture of the monoglyceride and diglyceride of oleic acid obtainable by esterification of glycerol with 1 to 2 mold of olein;

(c) about 5% by wt. of a mixture of the monoglyceride and diglyceride of palmitic acid, the monoglyceride and diglyceride of stearic acid, or the monoglycerides and diglycerides of palmitic acid and stearic acid, obtainable by esterification of glycerol with 1 to 2 mols of technical grade stearin which consists essentially of palmitic acid and stearic acid; and about 5% by wt. of an adduct of 5 mols ethylene oxide and soysterol.

2. A cosmetic composition for softening the skin comprising an effective amount of the lanolin substitute of claim 1 and a cosmetic carrier.

* * * * *

UNITED STATES PATENT AND TRADEMARK OFFICE
CERTIFICATE OF CORRECTION

PATENT NO. : 4,868,220

DATED : September 19, 1989

INVENTOR(S) : Ingeborg Scheuffgen

It is certified that error appears in the above-identified patent and that said Letters Patent is hereby corrected as shown below:

At Claim 1, Column 9, line 3, "mold" should read --mol$\underline{s}$--.

Signed and Sealed this

Twentieth Day of August, 1991

Attest:

HARRY F. MANBECK, JR.

*Attesting Officer*  *Commissioner of Patents and Trademarks*